(12) United States Patent
Aghajan

(10) Patent No.: US 6,614,924 B1
(45) Date of Patent: Sep. 2, 2003

(54) ADAPTIVE MASK TECHNIQUE FOR DEFECT INSPECTION

(75) Inventor: Hamid K. Aghajan, Palo Alto, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/365,583

(22) Filed: Aug. 2, 1999

(51) Int. Cl.⁷ .................................................. G06K 9/00
(52) U.S. Cl. ...................... 382/149; 382/144; 382/151; 382/168; 382/203; 382/260
(58) Field of Search ................... 382/149, 144, 382/151, 168, 164, 169, 171, 173, 199, 201, 203, 213, 260, 254, 266, 283, 275

(56) References Cited

U.S. PATENT DOCUMENTS

| | | | |
|---|---|---|---|
| 5,548,326 A | * 8/1996 | Michael | 348/126 |
| 5,568,563 A | * 10/1996 | Tanaka et al. | 382/144 |
| 5,638,465 A | * 6/1997 | Sano et al. | 382/281 |
| 5,764,792 A | * 6/1998 | Kennealy | 382/133 |
| 5,807,647 A | * 9/1998 | Hashimoto | 430/30 |
| 5,808,735 A | * 9/1998 | Lee et al. | 356/237.2 |
| 5,982,927 A | * 11/1999 | Koljonen | 382/168 |
| 6,178,257 B1 | * 1/2001 | Alumot et al. | 382/145 |
| 6,252,981 B1 | * 6/2001 | Guest et al. | 382/149 |
| 6,269,194 B1 | * 7/2001 | Nichani | 382/270 |
| 6,282,309 B1 | * 8/2001 | Emery | 382/145 |
| 6,285,397 B1 | * 9/2001 | Webb et al. | 348/189 |
| 6,288,782 B1 | * 9/2001 | Worster et al. | 356/394 |

* cited by examiner

*Primary Examiner*—Bhavesh M. Mehta
*Assistant Examiner*—Sheela Chawan
(74) *Attorney, Agent, or Firm*—Skjerven Morrill MacPhearson LLP.; Michael B. Einschlag

(57) ABSTRACT

A two-dimensional scatter plot is created by plotting the gray levels of pixels from a test image against the gray levels of corresponding pixels from a reference image. A noise reduction filter is applied on the scatter plot to define a mask shape which can be extracted and filled-in to generate a mask. Defect pixels on the test image are identified by comparing corresponding pixel gray values against the mask. A typical application is detecting defects in a semiconductor wafer during device fabrication.

10 Claims, 18 Drawing Sheets

ADAPTIVE MASK TECHNIQUE FOR DEFECT INSPECTION

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(e).

BACKGROUND OF THE INVENTION

1. Field of the Invention

This invention generally relates to digital image processing and, more particularly, to systems and methods for detecting defects in a semiconductor device using image comparison techniques.

2. Description of the Related Art

Image comparison techniques are used to detect defects in a semiconductor wafer. Typically, a test image is acquired and then compared to a reference image. A defect-detection algorithm is then used to detect variations between the images and to determine whether such variations are real defects. In the so-called random-logic inspection mode, an image of a first die is acquired and then compared to the image of a second die in the same wafer. Array-inspection mode is similarly performed except that a section of a die is compared to another section in the same die having an identical structure. Array-inspection mode is used, for example, in testing devices with repeating structures such as memory cells. In lieu of comparing images from a wafer being tested, defects may also be detected by comparing an acquired test image with a known good image from a database.

FIG. 1 illustrates a defect detection method in the prior art. A test image and a reference image of the wafer feature being analyzed are acquired from different sections of the wafer using, for example, conventional electron-beam imaging techniques (step 110). Each image comprises a plurality of pixels, with each pixel being defined by its location within the image and its intensity or gray level. The use of gray levels in image processing is known in the art and is described in R. C. Gonzales and R. E. Woods, "Digital Image Processing," Addison-Wesley (1992), e.g. pages 6–7, which is incorporated herein by reference in its entirety. The two images are then aligned pixel-by-pixel such that each feature in the test image matches up with the corresponding feature in the reference image (step 120). A difference image is then generated by subtracting the gray levels of the two images (step 130). Because matching pixels with identical gray levels will be subtracted out, the difference image represents pixel gray level variations between the reference image and the test image. The gray level of each pixel in the difference image is scaled, normalized, and then plotted in a one dimensional histogram such as histogram 200 shown in FIG. 2 (step 140). Histogram 200 plots the number of pixels in the difference image having a specific gray level. For instance, histogram 200 indicates that there are 20,000 pixels in the difference image having a gray level of 50.

A pixel from the test image can be different from a corresponding pixel in the reference image even if there are no defects in the two images. Intensity variations can be caused by, for example, differences in the physical layer structures, noise in the image acquisition electronics and signal paths, and varying noise modulation level within a single image across different gray levels. Thus, pixels in the difference image do not necessarily indicate that a defect exists. To differentiate real defects from false or "nuisance" defects, each pixel in the difference image is compared to a threshold window (FIG. 1, step 150). Pixels with a gray level outside the threshold window are declared defects. For example, if the threshold window is ±50 and a pixel in the difference image has a gray level of 60 (i.e. the gray levels of the test and reference images differ by 60 units), a defect event is declared (FIG. 1, step 160). The defect event is then verified by an operator to ensure that the die is indeed defective before the die is discarded in subsequent processing.

Finding the optimum threshold value for a given test image is an important but imprecise task. The threshold value must be chosen such that real defects are detected while differentiating nuisance defects. The narrower the threshold value, the more nuisance defects will be declared. Nuisance defects adversely affect production throughput because each defect event must be checked and verified. On the other hand, widening the threshold window will reduce nuisance defect events at the expense of letting real defects go undetected.

From the foregoing, a defect detection method which can detect real defects while minimizing the reporting of nuisance defects is highly desirable.

SUMMARY

A novel method and associated apparatus for detecting defects is disclosed. In an embodiment of the invention, a first image and a second image are provided and aligned. A first two-dimensional scatter plot is created by plotting the gray levels of the pixels from the first image against the gray levels of corresponding pixels from the second image. A second two-dimensional scatter plot is then created by filtering the data points of the first scatter plot. The second scatter plot provides a mask shape which can be extracted and filled-in to create a mask. Defects are identified by comparing the gray levels of corresponding pixels from the first and second images against the mask.

DETAILED DESCRIPTION

The present invention overcomes the limitations of defect detection methods in the prior art by using an adaptive thresholding scheme on a pair of images being analyzed. In contrast to prior art methods which use a predetermined threshold for all image pairs, this method uses a threshold mask which is adapted for each pair of images. The invention can be used in a variety of imaging applications including in electron-beam, bright-field, dark-field, laser, and atomic-force microscopy ("AFM") inspection systems.

Figure 1:
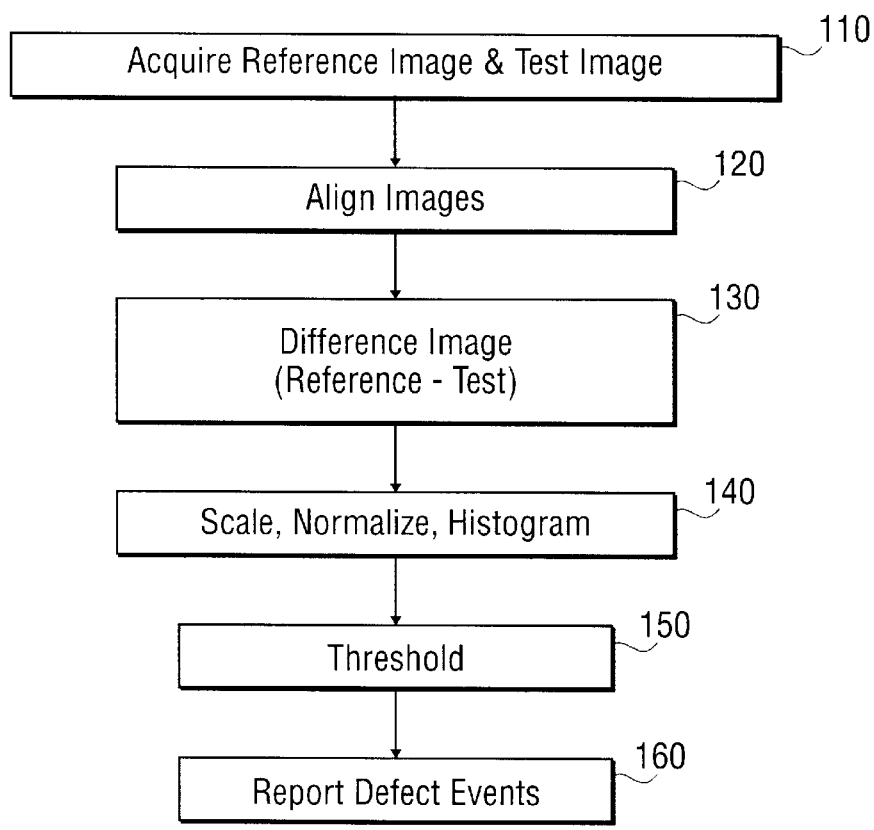
FIG. 1 shows a defect detection method in the prior art.
Figure 2:
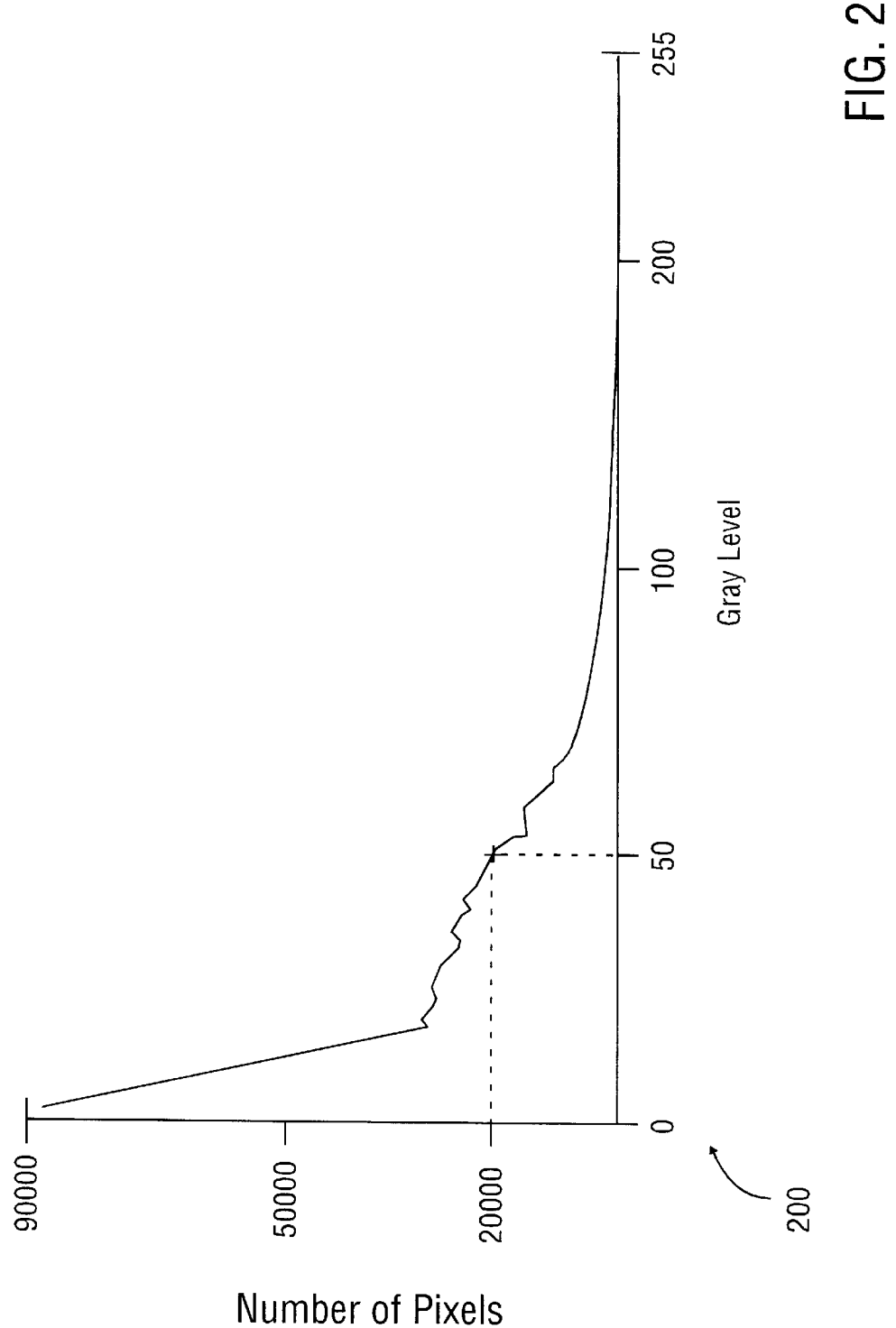
FIG. 2 shows a one-dimensional histogram plot of gray levels.
Figure 3:
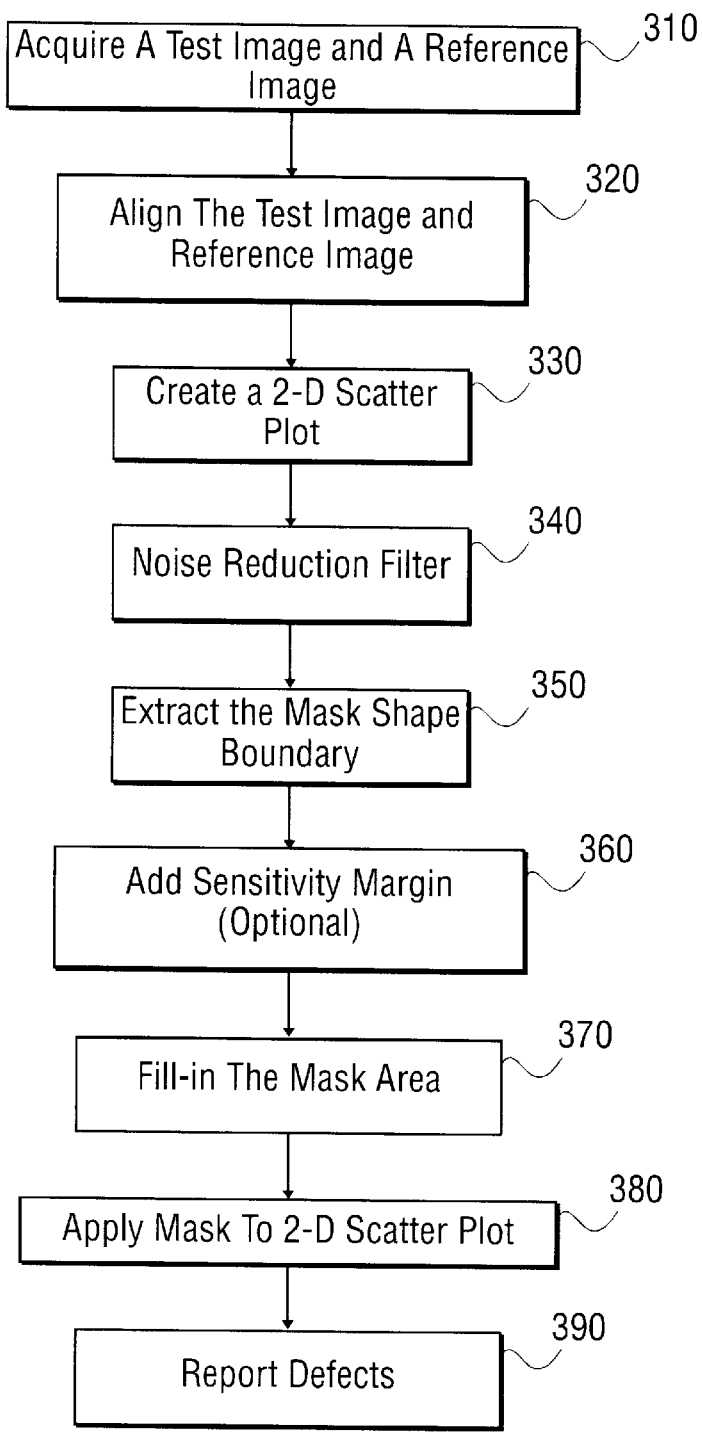
FIG. 3 shows the steps of an embodiment of the present invention.

FIG. 3 shows the steps of an embodiment according to the present invention. In step 310, a test image and a reference image of, for example, semiconductor structures are acquired using conventional image acquisition techniques. The images can also be acquired using the step-and-image acquisition system disclosed in commonly-owned U.S. patent application Ser. No. 09/226,967, "Detection of Defects In Patterned Substrates," filed Jan. 8, 1999, which is incorporated herein by reference in its entirety.

In step 320, the test and reference images are aligned to match up corresponding pixels between the two images. A variety of alignment techniques can be used with the present invention including the technique disclosed in commonly-owned U.S. patent application Ser. No. 09/227,747, "Feature-Based Defect Detection," filed Jan. 8, 1999, which is incorporated herein by reference in its entirety. The alignment step is required to ensure that every feature in the test image will be compared to an equivalent feature in the reference image.

Figure 4A:
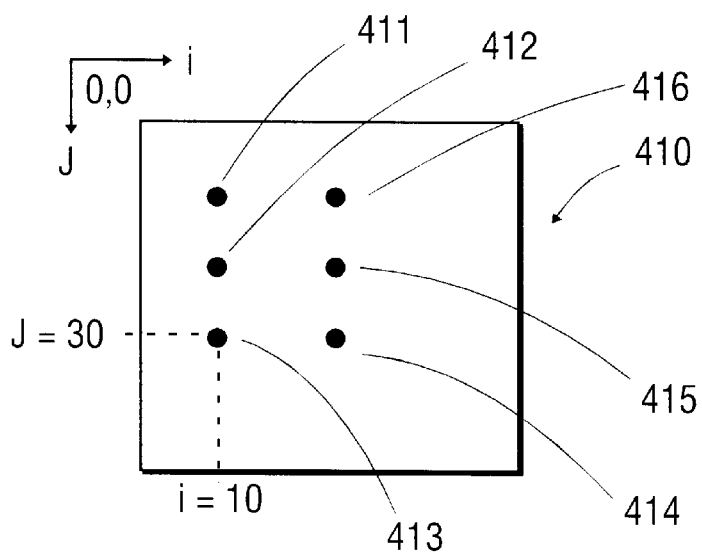
FIGS. 4A–4c show an alignment step in accordance with the present invention.
Figure 4B:
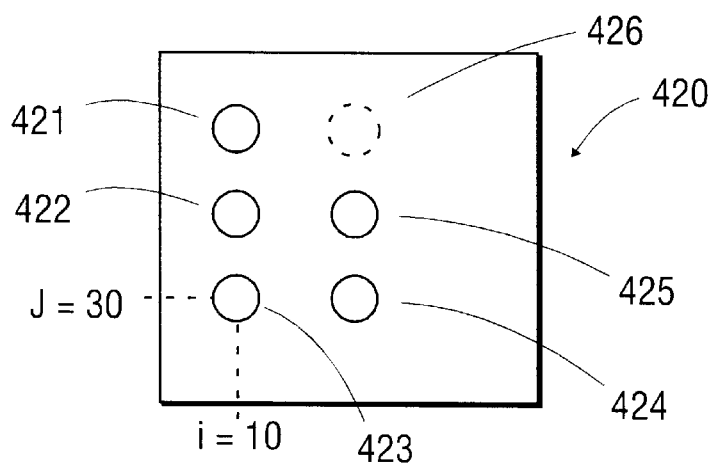
Figure 4C:
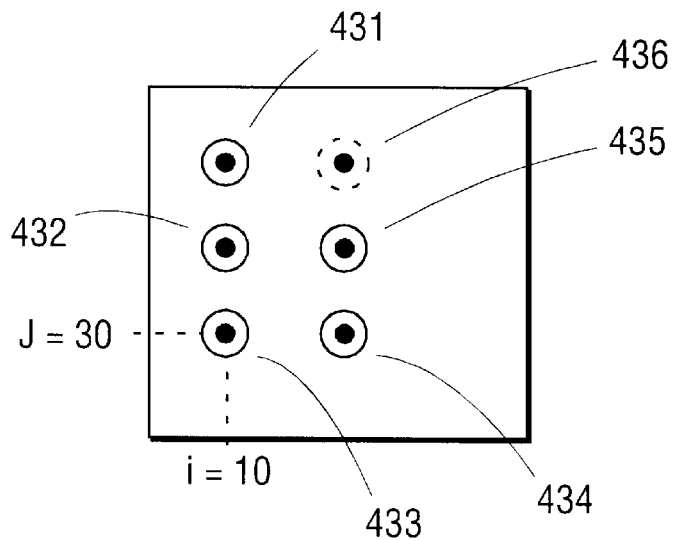

Step 320 is further illustrated in FIGS. 4A–4C. FIG. 4A shows a test image 410 comprising pixels 411–416. Each pixel is defined by its gray level and its location on the image. As an example, pixel 413 is on location i=10 and j=30 (i.e. (10,30)). The gray level of pixel 413 is 50 for purposes of this illustration. Table 1 provides the coordinate location and gray level for each pixel of test image 410 while Table 2 provides the same information for pixels 421–426 of reference image 420 (FIG. 4B).

TABLE 1

| Pixel | Location (i, j) | Gray Level |
|---|---|---|
| 411 | (10,10) | 100 |
| 412 | (10,20) | 150 |
| 413 | (10,30) | 50 |
| 414 | (20,30) | 180 |
| 415 | (20,20) | 200 |
| 416 | (20,10) | 250 |

TABLE 2

| Pixel | Location (i, j) | Gray Level |
|---|---|---|
| 421 | (10,10) | 100 |
| 422 | (10,20) | 150 |
| 423 | (10,30) | 50 |
| 424 | (20,30) | 150 |

TABLE 2-continued

| Pixel | Location (i, j) | Gray Level |
|---|---|---|
| 425 | (20,20) | 100 |
| 426 | (20,10) | 0 |

FIG. 4C graphically illustrates the alignment of test image 410 with reference image 420. Aligned pixel location 431 comprises the pixels 411 and 421, aligned pixel location 432 comprises the pixels 412 and 422, and so on.

Figure 5:
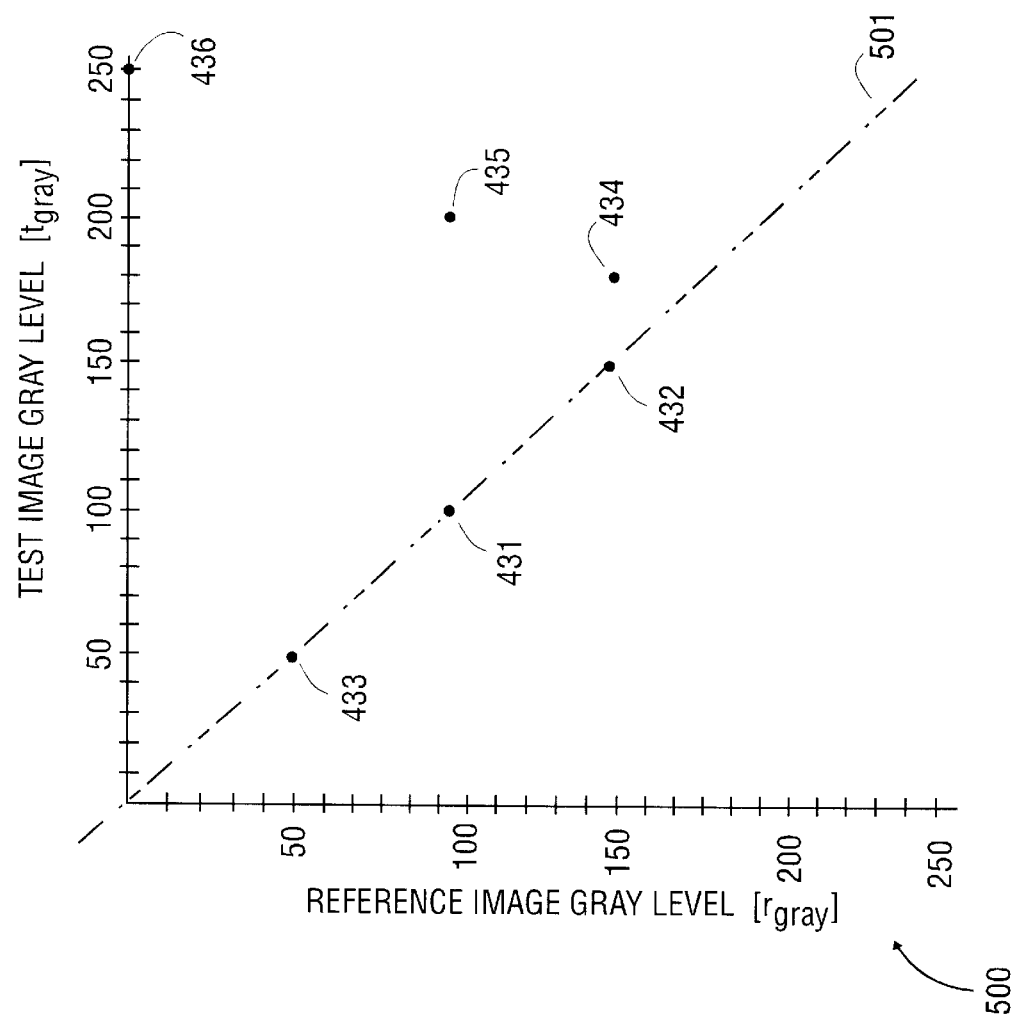
FIG. 5. shows a two-dimensional scatter plot in accordance with the present invention.

Once the reference and test images are aligned, the pixel-to-pixel correspondence between the test image and the reference image is known. A two-dimensional ("2D") scatter plot is created by plotting the gray level of a pixel from the test image against the gray level of the corresponding pixel in the reference image for each aligned pixel location (FIG. 3, step 330). Using FIG. 4C as an example, the gray level of pixel 411 is plotted against the gray level of pixel 421, the gray level of pixel 412 is plotted against the gray level of pixel 422, and so on. Using step 330 for locations 431–436 yields the data shown in Table 3. The resulting two-dimensional scatter plot 500 is shown in FIG. 5.

TABLE 3

| Aligned Pixel Location | Test Image Gray Level | Reference Image Gray Level | Coordinates ($t_{gray}$, $r_{gray}$) |
|---|---|---|---|
| 431 | 100 | 100 | (100,100) |
| 432 | 150 | 150 | (150,150) |
| 433 | 50 | 50 | (50,50) |
| 434 | 180 | 150 | (180,150) |
| 435 | 200 | 100 | (200,100) |
| 436 | 250 | 0 | (250,0) |

Table 3 shows that aligned pixel locations 434, 435, and 436 have varying gray levels and, thus, indicate the presence of possible defects. Locations 431, 432, and 433 are free of defects because the test image and the reference image have the same gray levels in said locations. Scatter plot 500 (FIG. 5) provides information as to the presence of possible defects. All aligned pixel locations with the same gray levels can be represented in scatter plot 500 by an imaginary line 501. The slope of imaginary line 501 is +1 because it represents the aligned pixel locations wherein the gray level of the test image pixel is the same as the gray level of the corresponding pixel in the reference image. All aligned pixel locations with varying gray levels will lie away from imaginary line 501. The further a location is plotted away from line 501, the greater the deviation in gray levels, and the higher the chance that a defect exists in that location. In scatter plot 500, locations 434, 435, and 436 are not on imaginary line 501 and indicate the presence of possible defects. In this disclosure, the shorthand ($t_{gray}$, $r_{gray}$) will be used to indicate the coordinates of a 2D scatter plot data point to distinguish it from an image pixel location, which coordinate is indicated by the shorthand (i,j). For example, aligned pixel location 435 is defined as a 2D scatter plot data point in location (200,100).

A pseudo code for implementing a two-dimensional scatter plot in computer software is shown below. In the pseudo code, the gray level values are plotted in a memory array variable ("Scatter").

```
/* PSEUDO CODE FOR CREATING A 2D SCATER PLOT */
Acquire Reference Image;
Acquire Test Image;
Align Test Image to Reference Image;
Create a 256x256 Image named Scatter;
Initialize Scatter to 0;
Do for i = 1 to NumRows
{
    Do for j = 1 to NumCols
    {
        p1 = Reference(i,j);
        p2 = Test(i,j);
        Scatter(p2,p1) = 1;
    }
}
Plot Scatter as an Image;
/* END OF PSEUDO CODE */
```

2D scatter plots are also disclosed by the same inventor in commonly-owned U.S. patent application Ser. No. 09/365,517 "Two-Dimensional Scatter Plot Technique For Defect Inspection,", which is incorporated herein by reference in its entirety.

Figure 6:
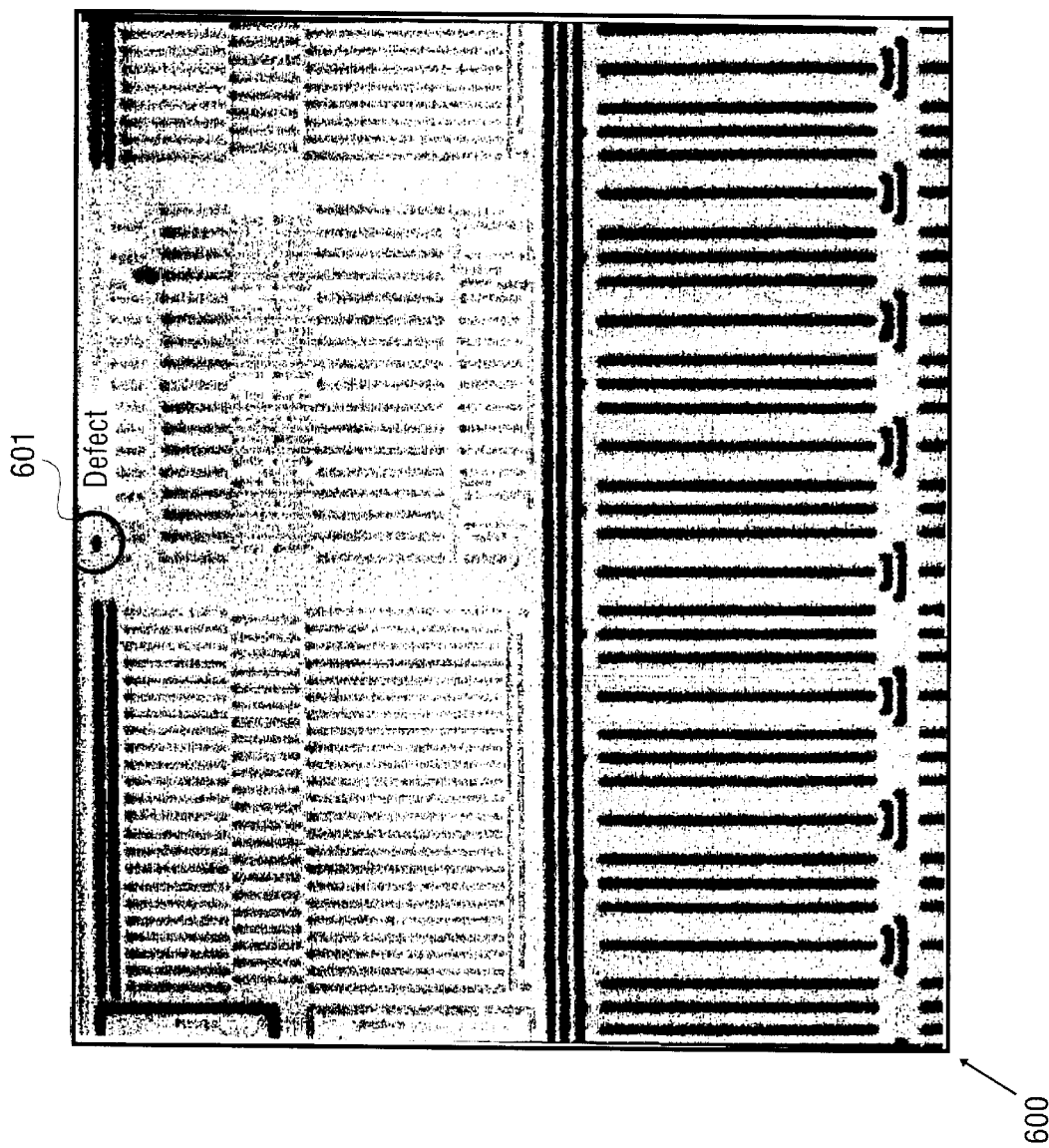
FIGS. 6–7 show a test image and a reference image, respectively, taken from a device wafer.
Figure 7:
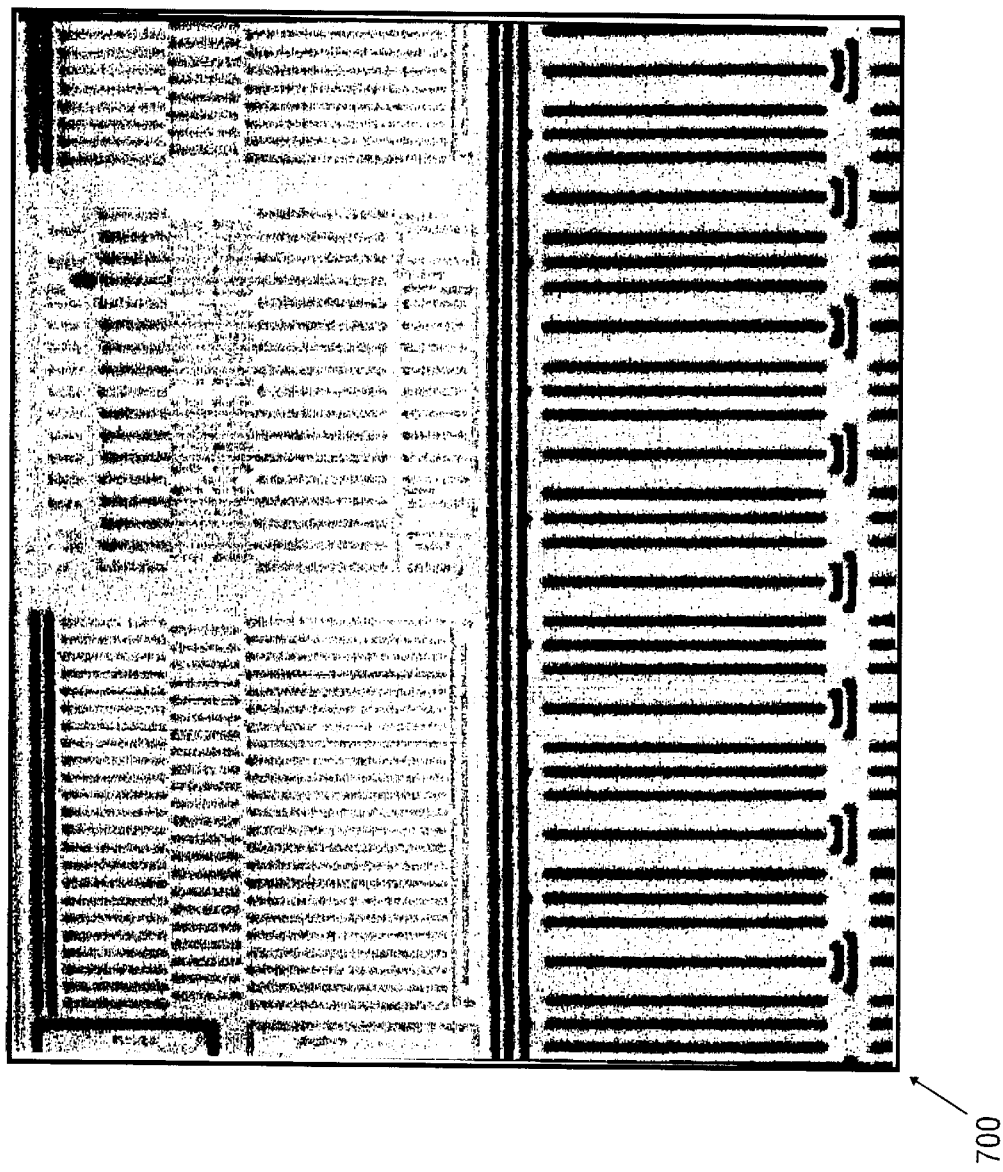
Figure 8:
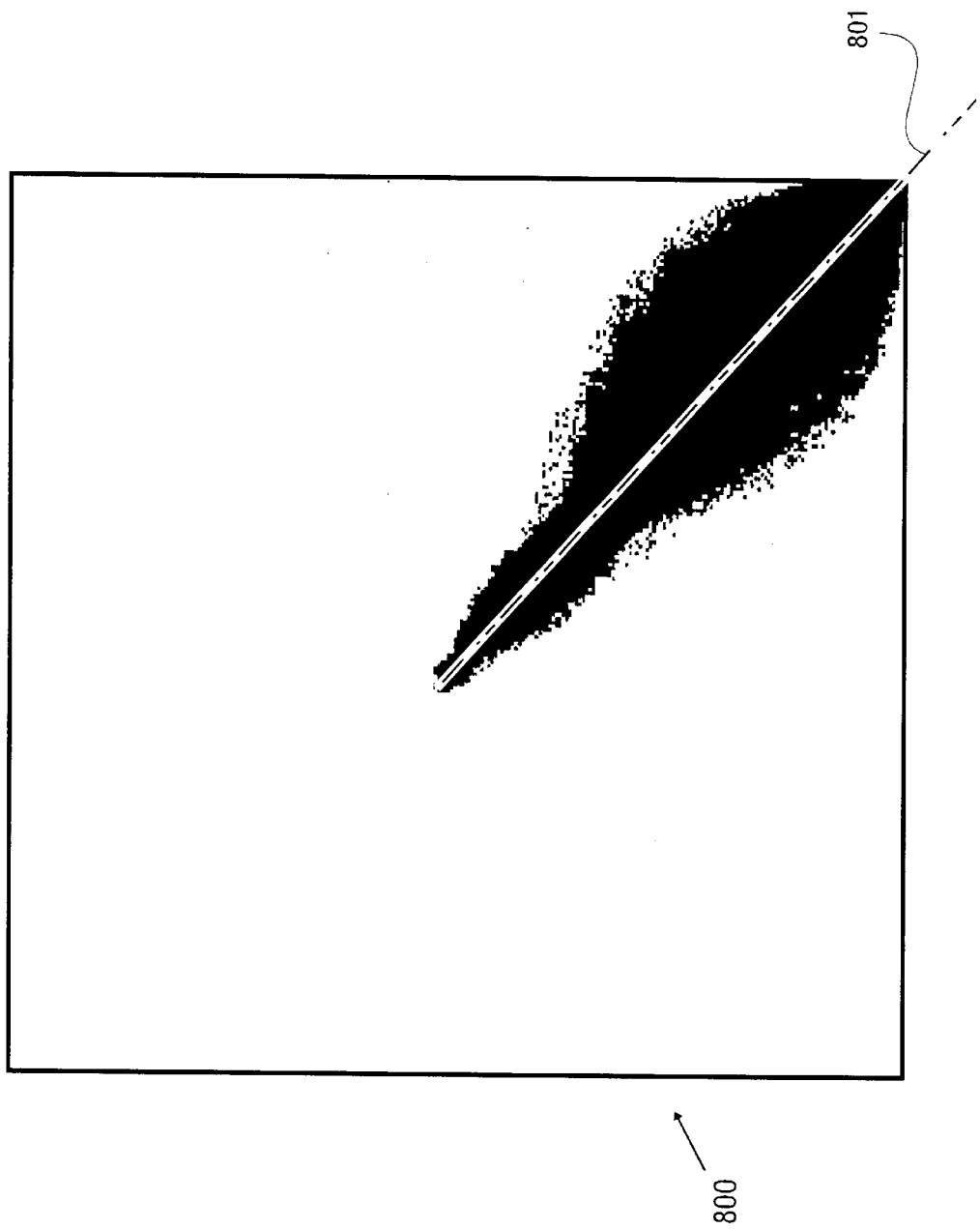
FIG. 8 shows a two-dimensional scatter plot in accordance with the present invention.

FIGS. 6–8 pictorially summarize steps 310, 320, and 330 of the embodiment shown in FIG. 3. FIG. 6 shows a test image 600 conventionally acquired from a wafer having a defect 601. A reference image 700 (FIG. 7) is acquired and then aligned (not shown) with test image 600. 2D scatter plot 800 (FIG. 8) is created by plotting the gray levels of pixels from the test image against the gray levels of corresponding pixels from the reference image. The scatter plot may be generated manually or by using a programmed computer. The data points of scatter plot 800 are plotted as white dots in a dark background. A line 801 defines the aligned pixel locations wherein the gray levels of the test and reference image pixels are identical. For example, if test image 600 was identical to reference image 700, all data points of scatter plot 800 would lie on line 801.

Scatter plot 800 contains gray level information for all pixels in the test and reference images, including pixels of defect 601. As previously discussed, the further a data point is from line 801, the more likely that the data point indicates the presence of a defect. The present method takes advantage of this information and builds a "mask" which can be "superimposed" on scatter plot 800 to differentiate defect pixels from good pixels. Data points outside the mask will be declared as defect events.

Figure 9A:
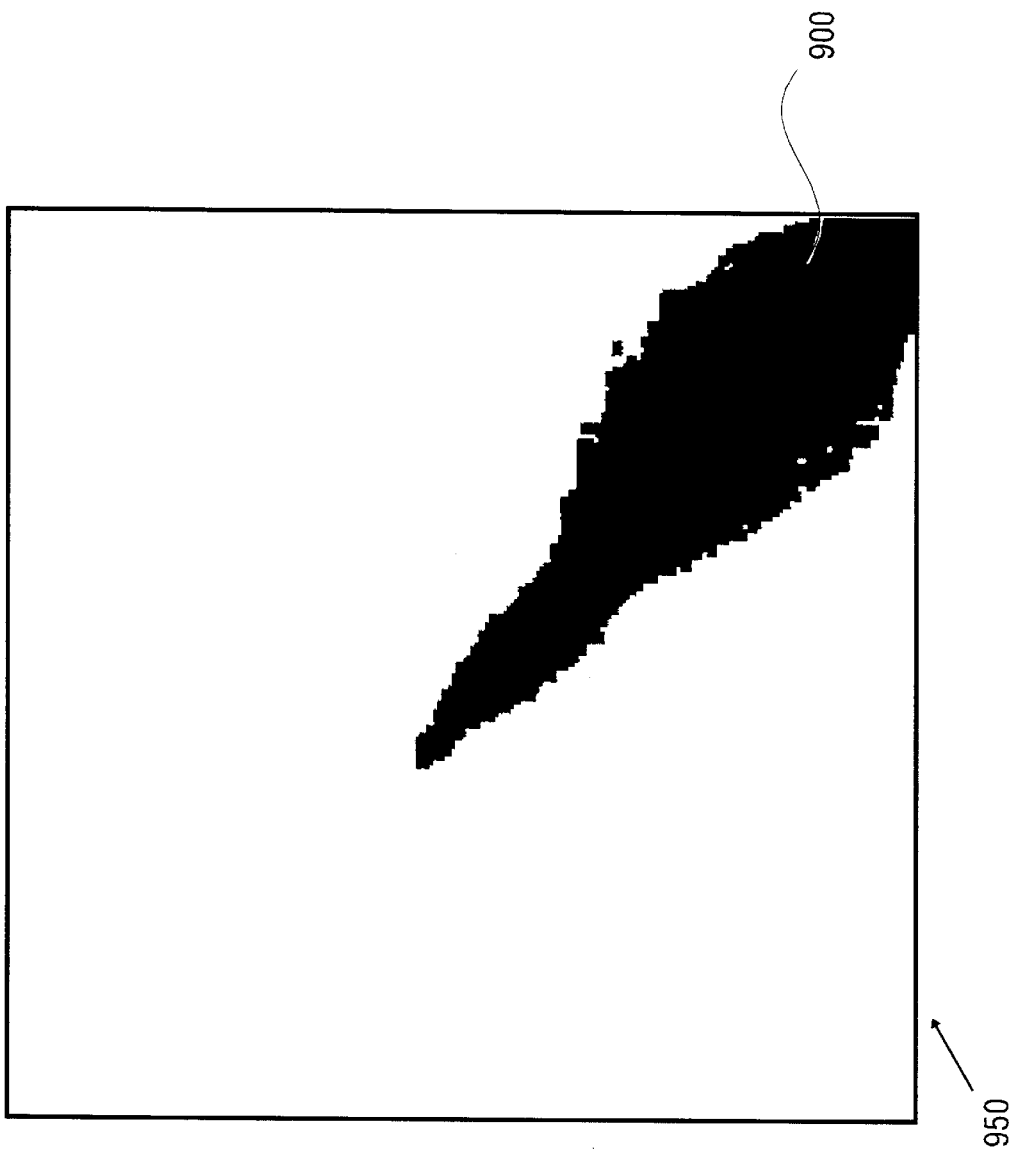
FIGS. 9A–9B show the result of using a morphological filter on the two-dimensional scatter plot shown in FIG. 8.

To find the profile or boundaries of the mask, a noise reduction filter is applied on the data points of scatter plot 800 (FIG. 3, step 340). A variety of conventional noise reduction filters may be used with the present invention including, for example, morphological filters. Morphological filters are known in the art and are described in B. Jahne, "Digital Image Processing Concepts, Algorithms, and Scientific Applications," Springer Verlag (1991), Chapter 11, and in R. C. Gonzales and R. E. Woods, "Digital Image Processing," Addison-Wesley (1992), Chapter 8, both of which are incorporated herein by reference in their entirety. Morphological filtering will "compact" and "clean-up" the data points of scatter plot 800 to define a mask shape. 2D scatter plot 950, shown in FIG. 9A, is the result of applying a morphological filter on scatter plot 800. Scatter plot 950 contains mask shape 900.

Figure 9B:
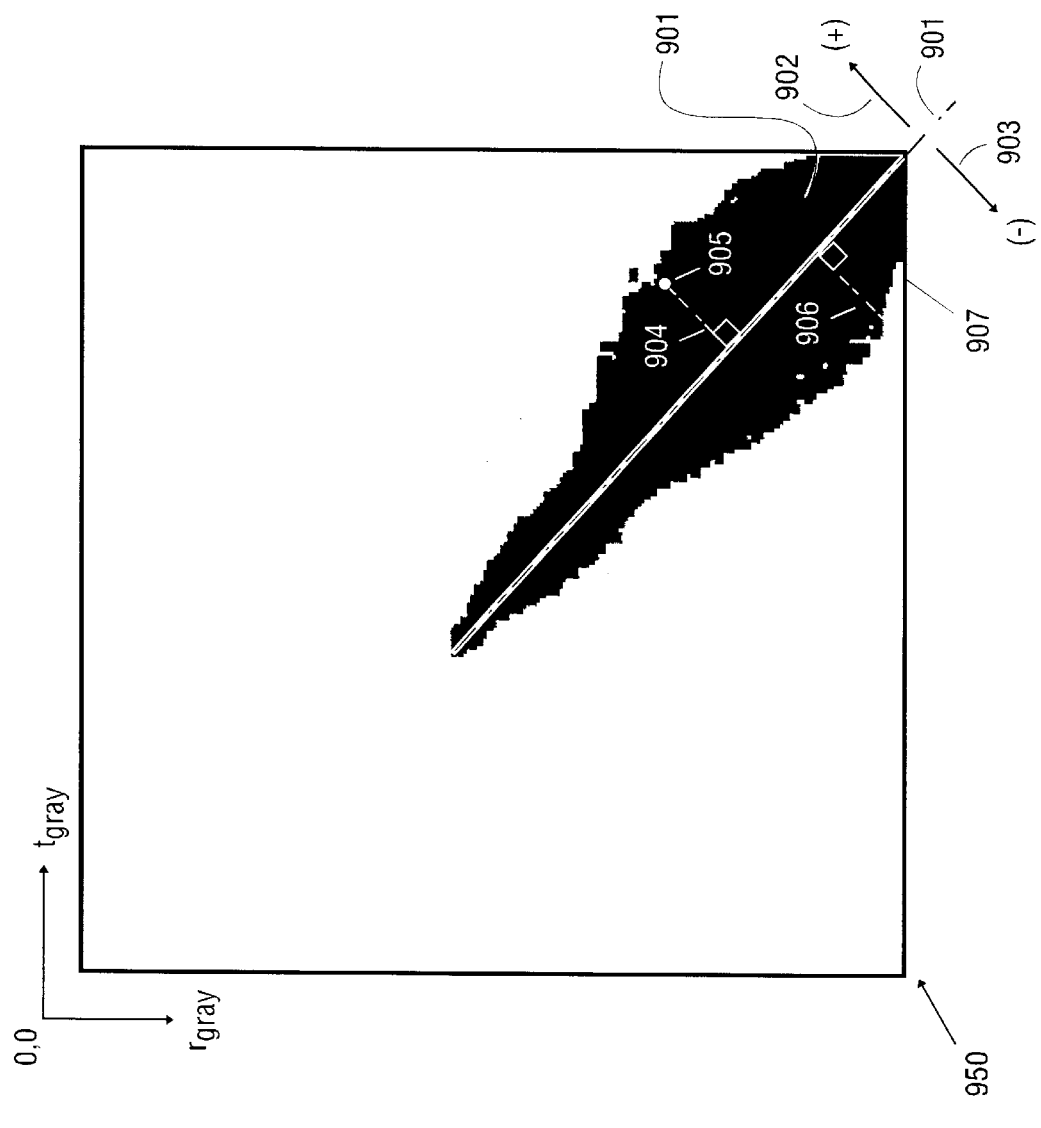

Boundary extraction is the process of obtaining the coordinates of each boundary data point of a mask shape (FIG. 3, step 350). One algorithm for extracting the boundary of mask shape 900 is as follows:

Algorithm For Extracting A Mask Shape (a1) As shown in FIG. 9B, create a line 901 which extends from the upper left hand corner to the bottom right hand corner of scatter plot 950.

(a2) Create two arrays of numbers for keeping track of perpendicular distances from line 901 to a boundary data point. Label one of the arrays as UPPER. UPPER is used to keep track of perpendicular distances of boundary points above line 901 (i.e. region indicated by arrow 902). The other array, LOWER, is used to keep track of perpendicular distances of boundary points below line 901 (region indicated by arrow 903). An example of a perpendicular distance is the length of perpendicular line 904 which extends from line 901 to a boundary point 905. Another example is the length of line 906 which is a perpendicular line extending from line 901 to boundary point 907.

(a3) Initialize all elements of arrays UPPER and LOWER to logic 0.

(a4) For each coordinate location ($t_{gray}$, $r_{gray}$,) on scatter plot 950, check if the coordinate has a data point. If it does, continue with steps (a5) to (a9); otherwise, go to the next location on the scatter plot. In FIGS. 8, 9A, and 9B, the data points are white points plotted on a dark background (i.e. a data point or logic 1 is plotted as a white dot while a logic 0 or absence of a data point is plotted as a black dot). Thus, the dark sections of FIG. 9B do not contain data points and will be ignored.

(a5) If the scatter plot location has a data point, measure its perpendicular distance, $D_{perp}$, from line 901. Also calculate the location of this data point, $R_{profile}$, along a one-dimensional ("1D") distance profile. 1D distance profiles will be described further below. $R_{profile}$ can be calculated using Eq. 1.

$$R_{profile}=(t_{gray}+r_{gray})/2 \qquad \text{(Eq. 1)}$$

(a6) If coordinates ($t_{gray}$, $r_{gray}$) is above line 901, $D_{perp}$ is assigned a positive value. Otherwise, $D_{perp}$ is negative.

(a7) If $D_{perp}$ is greater than the perpendicular distance currently stored in element $R_{profile}$ of array UPPER, store $D_{perp}$ in element $R_{profile}$ of UPPER.

(a8) If $D_{perp}$ is less than the perpendicular distance currently stored in element $R_{profile}$ of array LOWER, store $D_{perp}$ in element $R_{profile}$ of LOWER.

(a9) Continue for all data points.

Figure 10A:
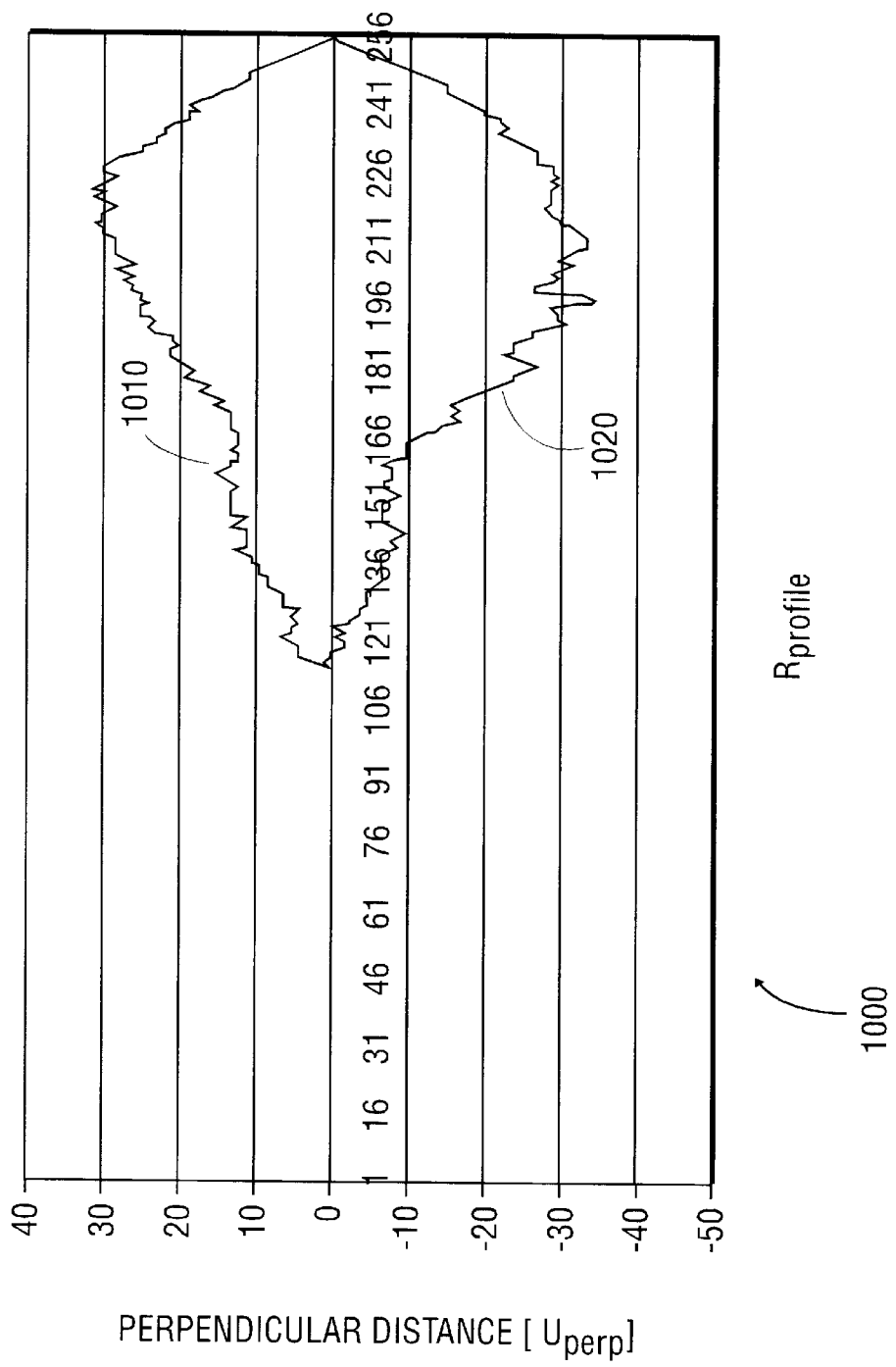
FIGS. 10A–10C show one-dimensional distance profiles in accordance with the present invention.
Figure 10B:
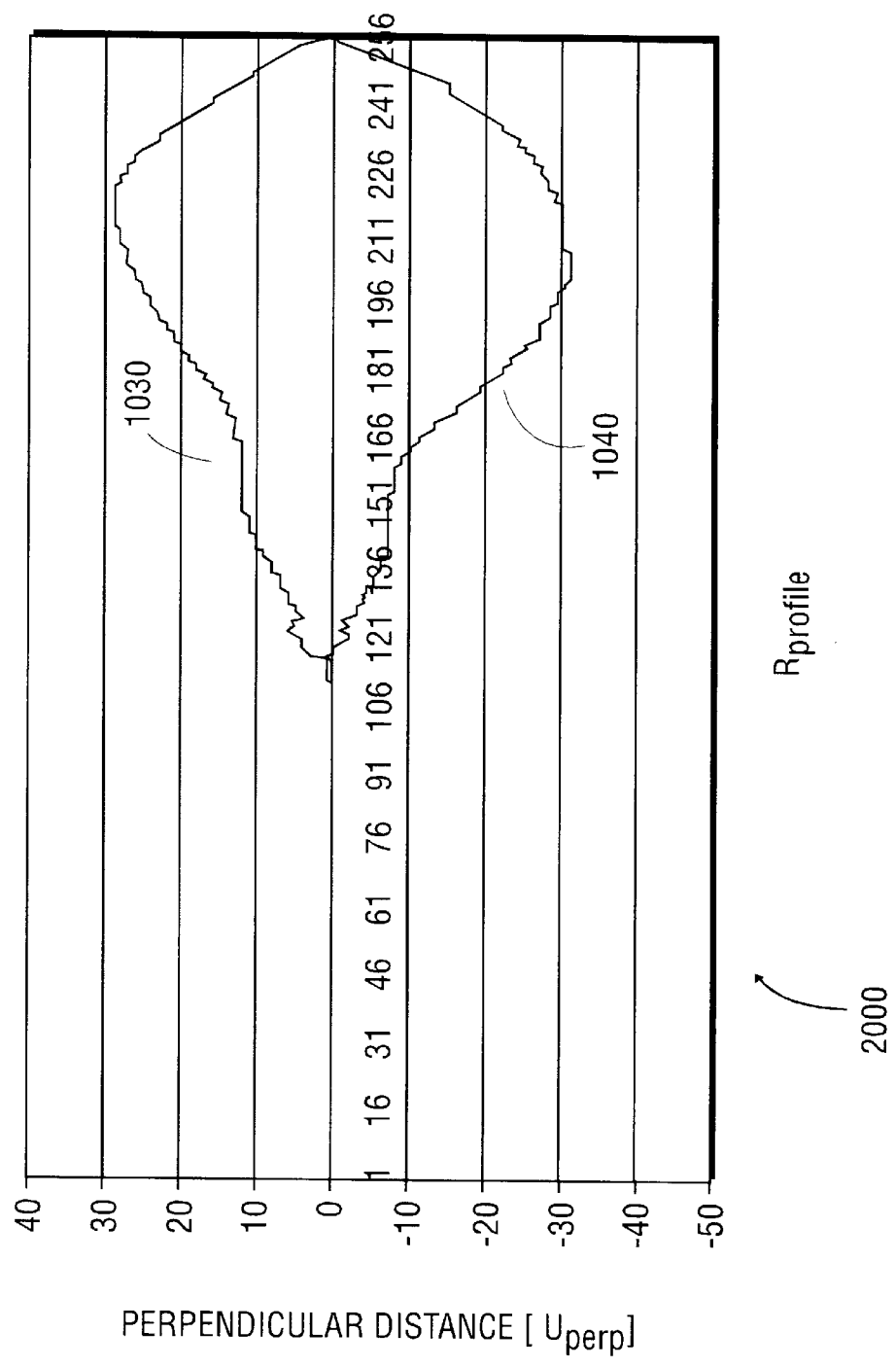

After performing the above mask shape extraction algorithm, arrays UPPER and LOWER will contain the perpendicular distances of the mask shape boundary points. The perpendicular distances and their corresponding $R_{profile}$ can be used to create a 1D distance profile 1000 shown in FIG. 10A. Curve 1010 is the graph of perpendicular distances stored in elements $R_{profile}$ of array UPPER while curve 1020 is a similar graph for array LOWER. To further delineate the extracted mask shape, distance profile 1000 can be smoothed using, for example, a moving average algorithm. Moving average algorithms are known in the art and are described in A. V. Oppenheim and R. W. Schafer, "Discrete-Time Signal Processing," Prentice-Hall (1989), which is incorporated herein by reference in its entirety. Distance profile 2000, shown in FIG. 10B, is the result of using a moving average algorithm on distance profile 1000. Curves 1030 and 1040 are the moving averages of curves 1010 and 1020, respectively.

Figure 10C:
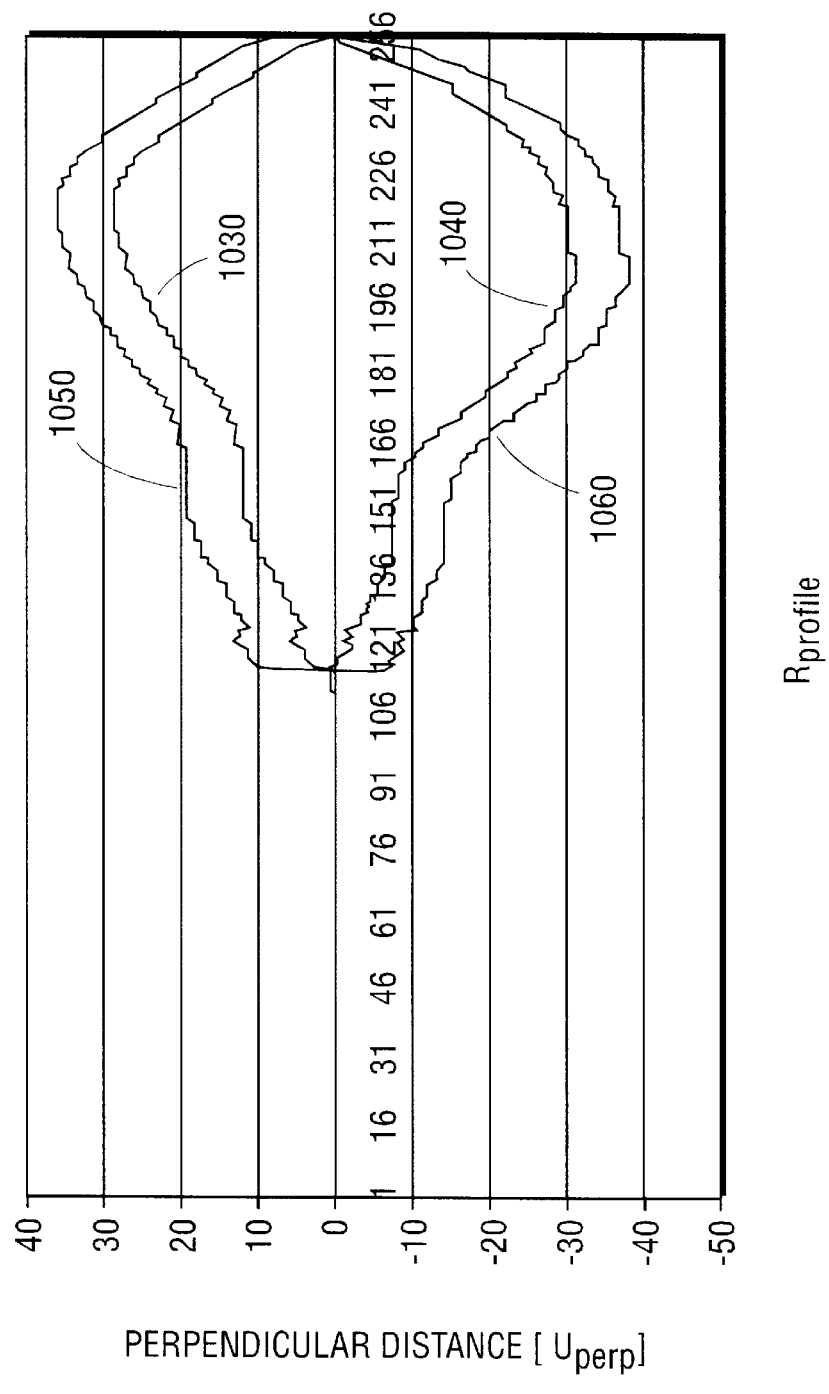

Optionally, a sensitivity margin can be applied on the extracted mask shape (FIG. 3, step 360) to allow a user to vary the extent of the mask. The user selected sensitivity value can be used to scale or offset the extracted mask shape. Curve 1050 in FIG. 10C shows the result of adding a sensitivity value, $S_{value}$, to each point of curve 1030. Curve 1060 is the result of subtracting $S_{value}$ from each point of curve 1040.

A mask look-up table is created by filling-in all coordinate locations within the boundary of the extracted mask shape (FIG. 3, step 370). An algorithm for filling-in the extracted mask shape will be illustrated using scatter plot 950 shown in FIG. 9B.

Algorithm For Filling-In A Mask Shape Area (b1) Create a two-dimensional scatter plot, $M_{scatter}$. Set all data points of $M_{scatter}$ to logic 1.

(b2) For each location ($t_{gray}$, $r_{gray}$) of scatter plot 950, calculate $R_{profile}$ using Eq. 1 and get the perpendicular distance $D_{perp}$.

(b3) Plot $R_{profile}$ and $D_{perp}$ in distance profile 2000 shown in FIG. 10B (or the distance profile shown in FIG. 10C if a sensitivity margin is used). If the point ($R_{profile}$, $D_{perp}$) is enclosed by curves 1030 and 1040, reset location ($t_{gray}$, $r_{gray}$) of $M_{scatter}$ to logic 0. Otherwise, continue to the next ($t_{gray}$, $r_{gray}$) location of scatter plot 950.

(b4) Continue for all locations.

Figure 11:
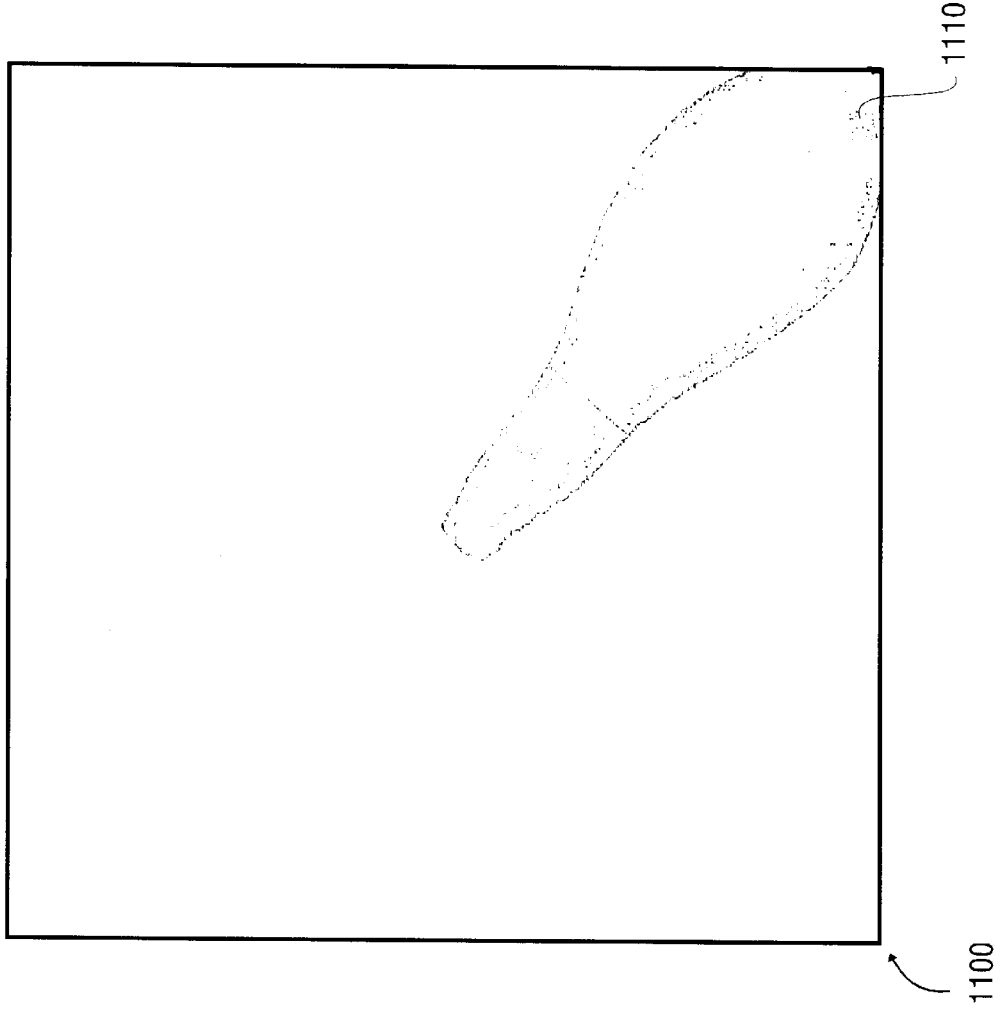
FIG. 11 shows a mask in accordance with the present invention.
Figure 12:
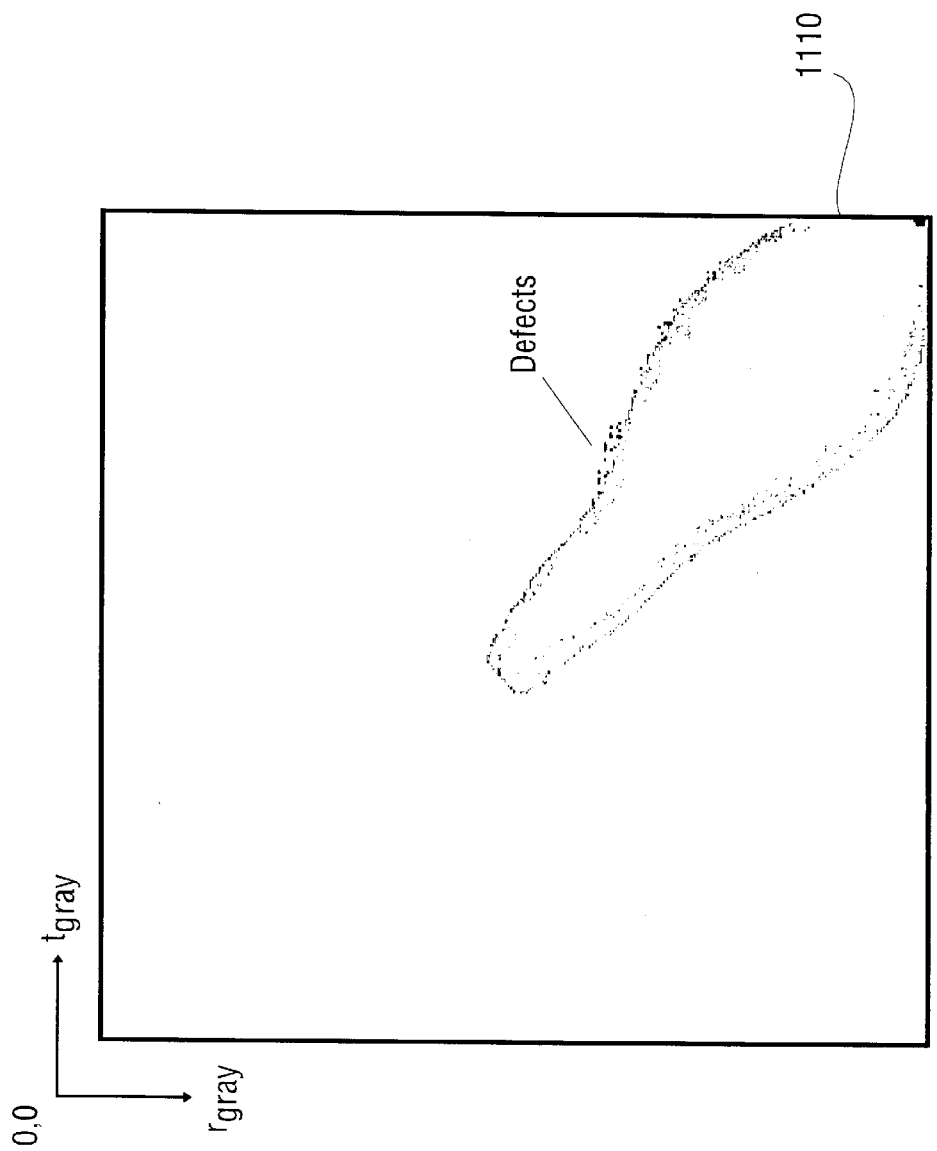
FIG. 12 shows a mask superimposed on an un-filtered two-dimensional scatter plot.

The above algorithm will result in an $M_{scatter}$ 1100 shown in FIG. 11. $M_{scatter}$ 1100 contains a mask 1110 which can be used to detect defect points in a two-dimensional scatter plot. All points inside mask 1110 are at logic "0". FIG. 12 shows mask 1110 superimposed on scatter plot 800. Data points outside the mask will be declared as defect events.

One algorithm for utilizing mask 1110 for detecting defects is as follows:

Algorithm For Detecting Defects Using A Mask (c1) For all pixels of a test image and a reference image, read the corresponding gray levels $t_{gray}$ and $r_{gray}$, respectively.

(c2) If location ($t_{gray}$, $r_{gray}$) of $M_{scatter}$ 1100 is a logic 0, this indicates that the location is inside the mask and, thus, there is no defect event. Continue to the next pixel of the test and reference images.

(c3) If location ($t_{gray}$, $r_{gray}$) of $M_{scatter}$ 1100 is a logic 1, the location is outside the mask and a defect exists. Report a defect event.

(c4) Continue for all pixel pairs of the test and reference images.

Appendix A provides further examples of how the present invention can be implemented. Appendix A lists the source code of a "C" programming language function in accordance with the present invention. The code would be executed by a computer or processor which is conventionally coupled to or a part of a defect inspection system. Of course, such a system would typically store this source code and the resulting plots, masks, etc. in a computer-readable medium (memory). Table 4 shows the correspondence between the steps of the invention and the source code listed in Appendix A.

TABLE 4

| C Function | Page in App. A | Step | Comment |
| --- | --- | --- | --- |
| hist2D8 | A/3 | 330 | 2D Scatter Plot |
| hist_2D8_open | A/3 | 340 | Morphological Filter |

TABLE 4-continued

| C Function | Page in App. A | Step | Comment |
| --- | --- | --- | --- |
| hist_2D8_1Dprofile | A/4 | 350 | Extract 1D profile and apply moving average. |
| hist_2D8_fitbound | A/5 | 360, 370 | Sensitivity margin and filling-in of mask |
| hist_2D8_thresh | A/6 | 380 | Check for defects (thresholding) |

Figure 13:
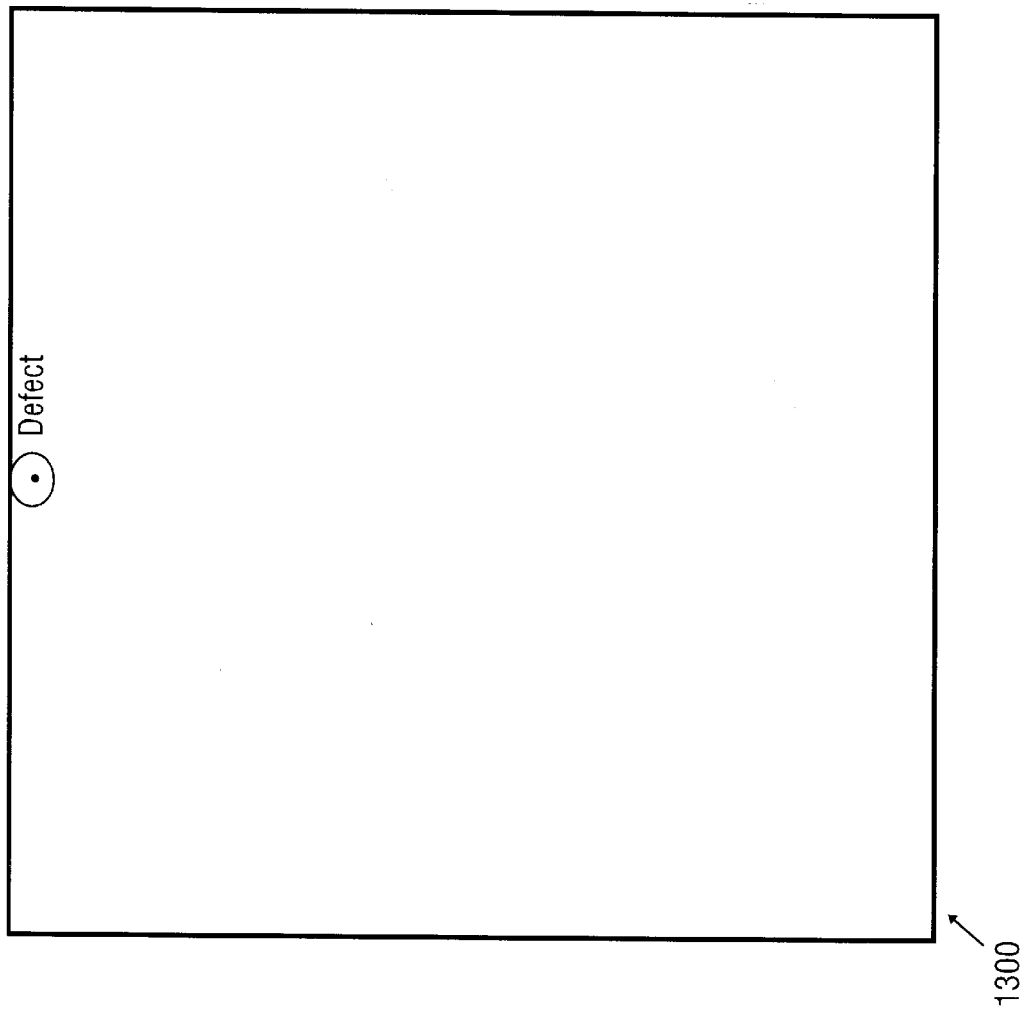
FIG. 13 shows a wafer defect map obtained using an adaptive mask.
Figure 14:
FIG. 14 shows a predetermined threshold superimposed on an un-filtered two-dimensional scatter plot.
Figure 15:
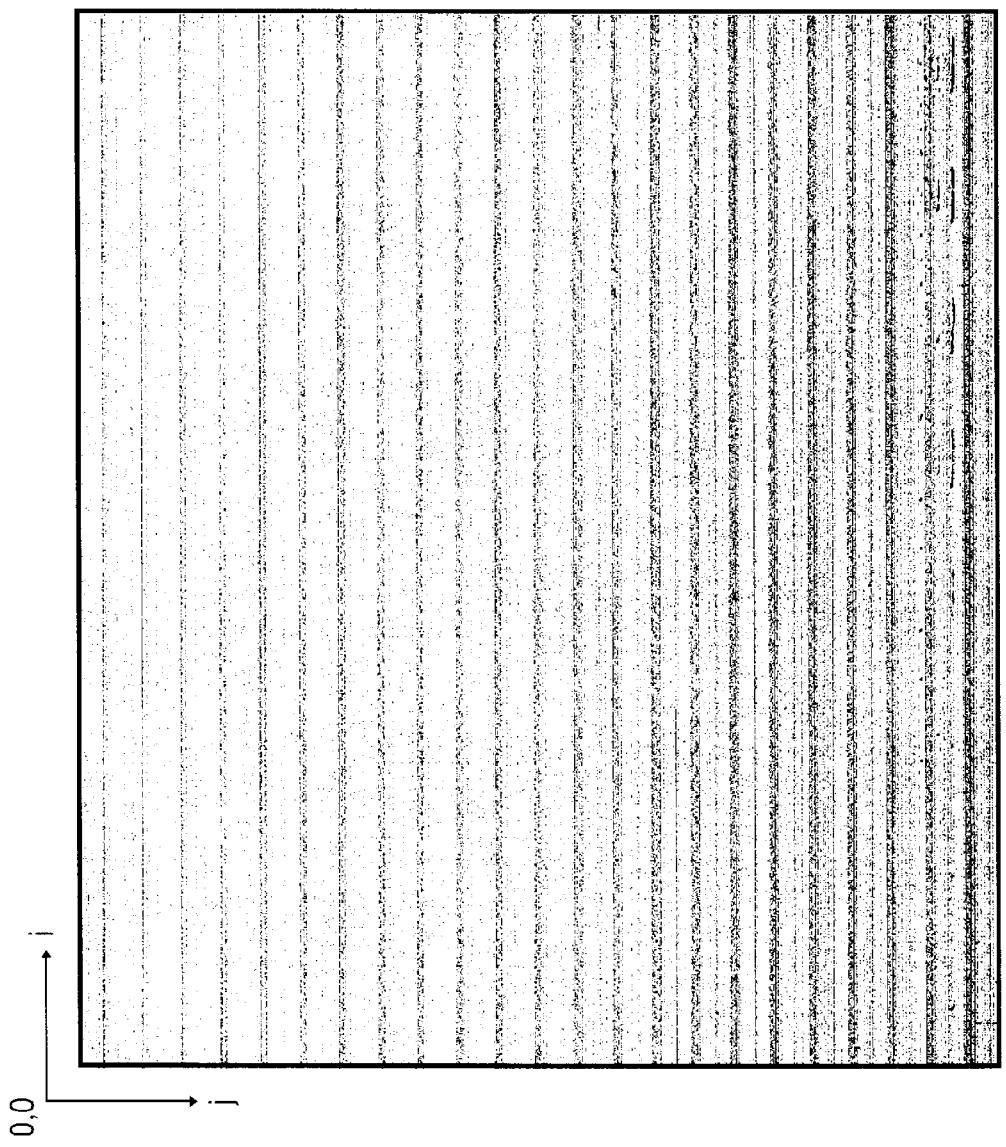
FIG. 15 shows a wafer defect map obtained using a predetermined threshold.

FIGS. 13 to 15 further demonstrate the effectiveness of the present method. Using $M_{scatter}$ 1100 to detect defects on scatter plot 800 using steps (c1)–(c4) results in a defect map 1300 shown in FIG. 13. Note that defect map 1300 correctly identifies defect 601 of test image 600 (FIG. 6).

FIG. 14 graphically shows the application of a predetermined threshold, defined by lines 1401 and 1402, on scatter plot 800. The use of predetermined thresholds is also disclosed by the same inventor in commonly-owned U.S. patent application Ser. No. 09/365,517, "Two-Dimensional Scatter Plot Technique For Defect Inspection," which is incorporated herein by reference in its entirety. Points that are not enclosed by lines 1401 and 1402 are declared as defect events. FIG. 15 shows a defect map resulting from the application of the predetermined threshold on scatter plot 800. Note that numerous nuisance defects were detected without catching defect 601.

It is to be understood that the description given above is for purposes of illustration and is not intended to be limiting. Numerous variations are possible without deviating from the scope and spirit of the invention. The invention is set forth in the following claims.

What is claimed is:

1. A method for detecting defects comprising:

(a) providing a first image of an object to be inspected and an associated second image;

(b) aligning the first image with the second image;

(c) creating a first plot by plotting gray levels of pixels from the first image against gray levels of corresponding pixels from the second image;

(d) creating a second plot by filtering the first plot;

(e) creating a mask, the mask having a profile defined by a shape of the second plot; and, (f) using the mask to detect defects represented in the first image.

2. The method of claim 1 wherein filtering is performed using a morphological filter.

3. The method of claim 1 wherein an extent to the mask is user adjustable.

4. The method of claim 1 further comprising using a moving average filter to smooth the profile of the mask.

5. The method of claim 1 wherein the second image is obtained from a database.

6. The method of claim 1 further comprising storing the first plot and the second plot in a computer-readable medium.

7. A computer-readable medium storing a program for carrying out the method of claim 1.

8. A computer-readable medium comprising:

a plurality of memory locations containing data representing a first image and an associated second image, said first and second images each having a plurality of pixels with each pixel being defined by a location coordinate and; a gray level;

a first array comprising a plurality of memory locations storing data defining a mask, the mask being created by: (a) aligning the first image with the second image, and (b) filtering a plot of the gray levels of pixels from the first image against the gray levels of corresponding pixels from the second image; and a second array comprising a plurality of memory locations storing data defining defects, the defects being determined by using the mask to detect defects represented in the first image.

9. The computer-readable medium of claim 8 wherein the filtering is performed using a morphological filter.

10. The computer-readable medium of claim 8 wherein a moving average algorithm is used to smooth the plot of the gray levels of pixels from the first image against the gray levels of pixels from the second image.

* * * * *